US00PP21788P2

(12) United States Plant Patent
Schmid

(10) Patent No.: US PP21,788 P2
(45) Date of Patent: Mar. 15, 2011

(54) ***MISCANTHUS* PLANT NAMED 'TIGER TAIL'**

(50) Latin Name: ***Miscanthus strictus*×*Miscanthus cosmopolitan***
Varietal Denomination: Tiger Tail

(76) Inventor: Thomas Schmid, Jackson, MI (US)

( * ) Notice: Subject to any disclaimer, the term of this patent is extended or adjusted under 35 U.S.C. 154(b) by 0 days.

(21) Appl. No.: 12/586,598

(22) Filed: Sep. 24, 2009

(51) Int. Cl.
*A01H 5/00* (2006.01)

(52) U.S. Cl. ..... Plt./384
(58) Field of Classification Search ..... Plt./384
See application file for complete search history.

*Primary Examiner*—Susan B McCormick Ewoldt
(74) *Attorney, Agent, or Firm*—Reising Ethington P.C.

(57) ABSTRACT

A cultivar of *Miscanthus sinensis* called 'Tiger Tail.' This cultivar is characterized by its long green leaves banded by yellow portions. It is tall in stature with thick, strict culms giving it an appearance of being tall and leafy throughout the growing season. The culms are green and less visible due to its color being similar to the leaf color.

4 Drawing Sheets

Latin name: *Miscanthus strictus*×*Miscanthus cosmopolitan.*

Varietal denomination: 'Tiger Tail'.

BACKGROUND

The invention relates to a cultivar of *Miscanthus strictus* and *Miscanthus cosmopolitan.* The cultivar is perennial, ornamental grass grown for landscape use and is adapted to be grown in cold climates.

The inventor discovered the new cultivar, hereinafter referred to by its cultivar name, 'Tiger Tail.' The inventor discovered 'Tiger Tail' in a cultivated area of his nursery in Jackson, Mich. 'Tiger Tail' was produced by open pollination of *Miscanthus strictus* and *Miscanthus cosmopolitan*. 'Tiger Tail' has been cultivated in the nursery for three years. During this period, the 'Tiger Tail' has successfully been reproduced asexually ten (10) times through division and has proven to be stable with each successive generation.

SUMMARY OF THE INVENTION

'Tiger Tail' has not been observed under all possible environmental conditions. It is quite possible that variations in the environment may alter the phenotype. Changes in the genotype are not, however, expected as 'Tiger Tail' has shown to be quite stable.

Observable traits of 'Tiger Tail' that are unique thereto, are new and distinct and include:

1. uniform banding of the leaf blades;
2. a heavy caliber culm that extends upright and hold the plant upright late in the season having a green color complementing the leaf blades;
3. blooms that occur in late summer through early fall;
4. a height of 5 to 7 feet tall;
5. each culm having approximately 12 to 14 leaves extending out therefrom in alternate directions.

DETAILED BOTANICAL DESCRIPTION

Figure 1:
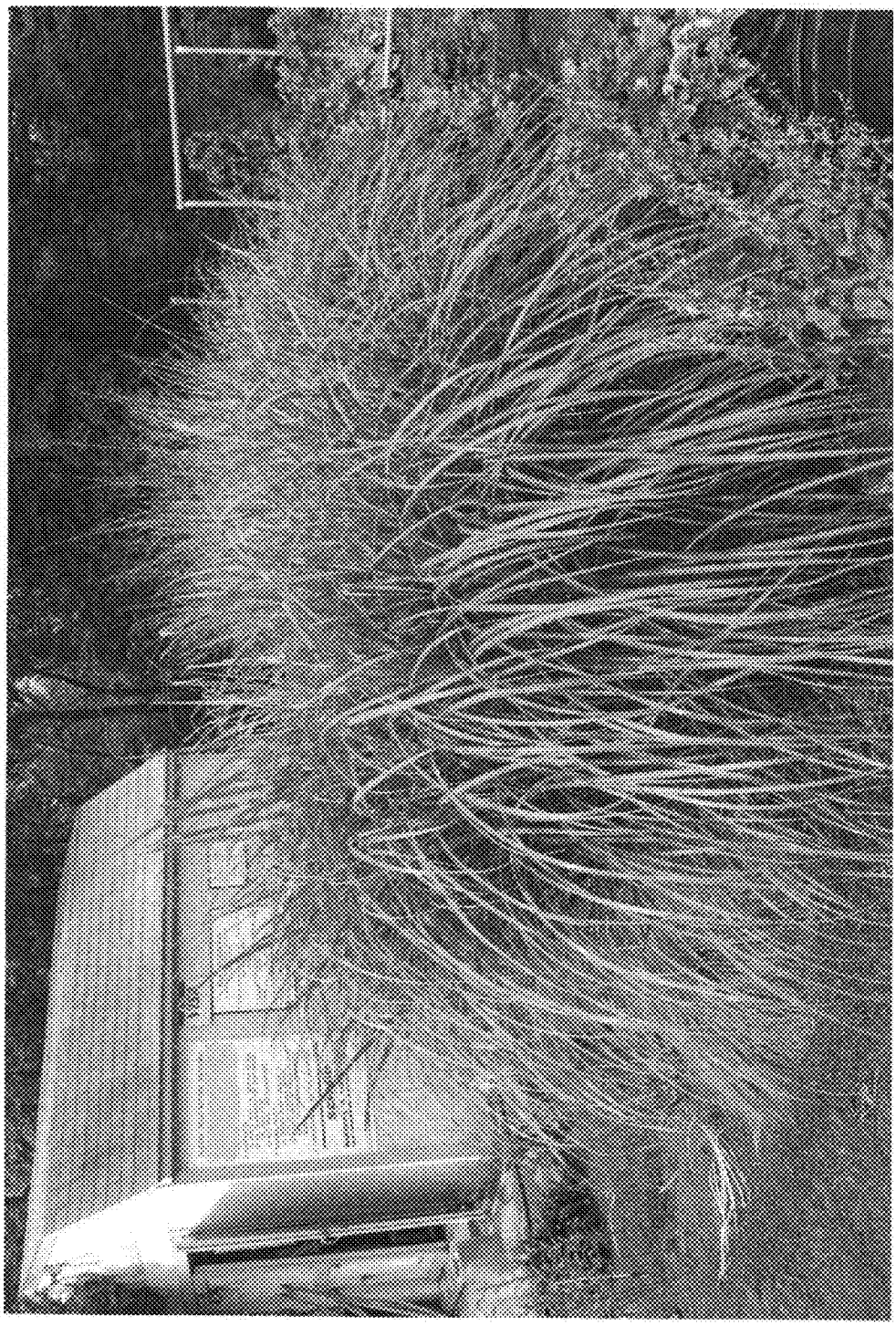
FIG. 1 shows the overall appearance of a mature 'Tiger Tail' in late Spring in its sixth year.
Figure 2:
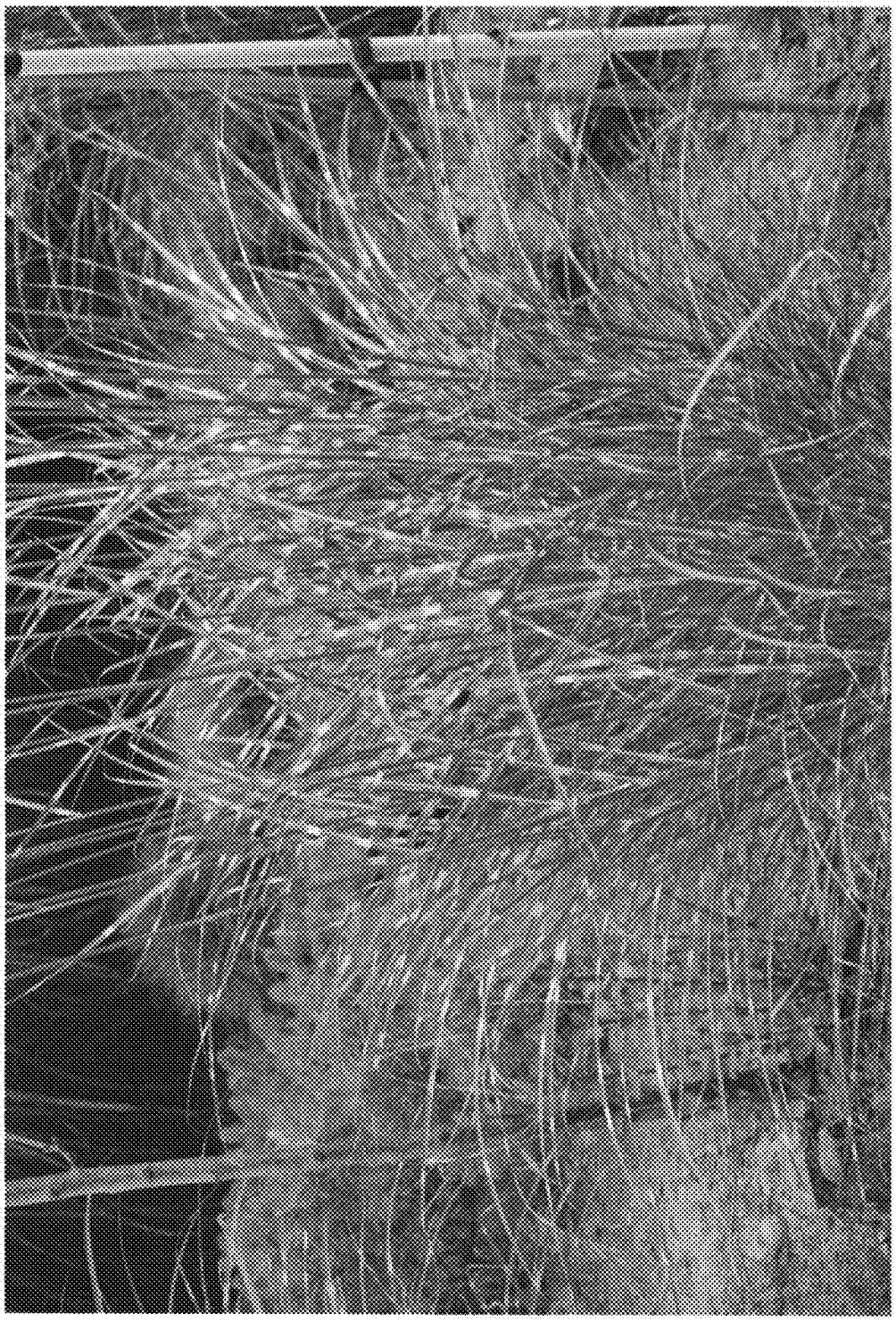
FIG. 2 is a photograph of a young 'Tiger Tail' asexually reproduced growing in the nursery to show the banding of the leaves and the culms and leaves shown in better detail.
Figure 3:
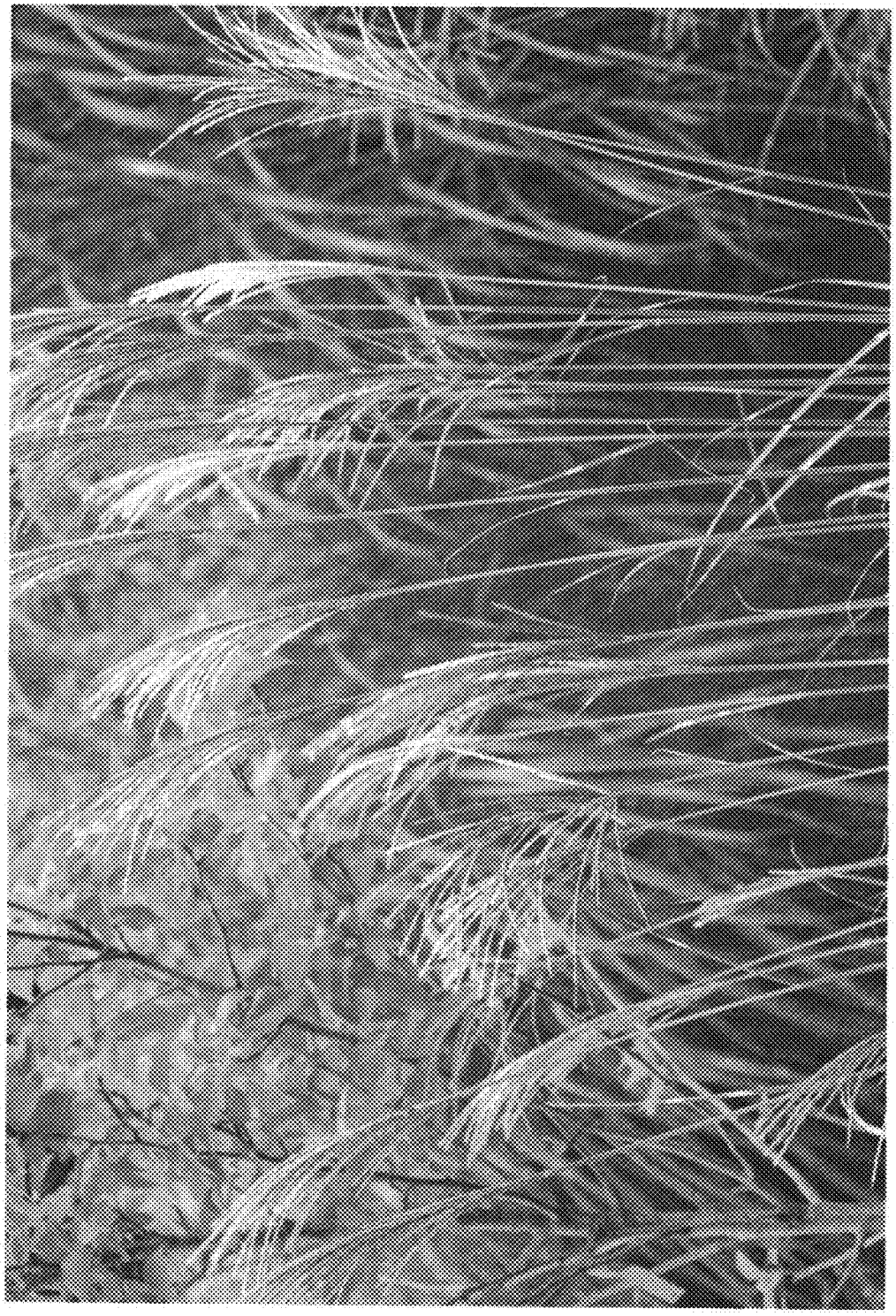
FIG. 3 is photograph of several blooms of a 'Tiger Tail.'

'Tiger Tail' has been grown outdoors for three years in Jackson, Mich. 'Tiger Tail' has been divided approximately ten times with each time producing a thriving plant. The colors indicated herein are according to The 2007 R.H.S. Colour Chart, Fifth Edition, of The Royal Horticultural Society, London, England, except where general color terms of ordinary dictionary significance are used.

'Tiger Tail' is the result of an open pollination between a *Mischantus strictus* and a *Miscanthus cosmopolitan*. 'Tiger Tail' has taken characteristics of both parents. From *Miscanthus strictus*, comes the spotted foliage and strict appearance. 'Tiger Tail' is uniquely different because while having a strict upright look, the leaves bend, giving it a more graceful and flowing appearance. The strict upright appearance of the leaves is attributed to *Mischantus strictus*, whereas the graceful, flowing bends to the leaves is attributed to *Miscanthus cosmopolitan.*

The culm is attributed to the *Miscanthus cosmopolitan*. These culm are not small wiry and unattractive as the *Miscanthus strictus* typically appear, but rather are fat and lush looking giving it a rich, robust and attractive look. None of the other varieties of *Miscanthus* have the combination of features as what is described herein.

Botanical classification: 'Tiger Tail' is a cultivar of *Miscanthus strictus*×*Miscanthus cosmopolitan.*

Common name: 'Tiger Tail' is a zebra grass.

General description:

*Blooming period.*—Generally blooms in September through the first part of October.

*Plant form.*—Herbaceous, clump-forming, ornamental grass with an upright, rigid culm and dense, bushy foliage.

*Height and spread.*—As high as 5 to 7 feet in height with a spread of approximately 4 feet in diameter (at the base) in three years growing time.

*Hardiness.*—Zones 4 through 9.

*Culture.*—Optimal growing occurs in fertile, moist soil in full sun. May tolerates shade when planted in hotter climates.

*Diseases.*—No known susceptibility to diseases has been observed to date.

*Pests.*—No known susceptibility to pests has been observed to date.

*Root description.*—Fibrous.

Culm description:

*General.*—Cylindrical, smooth, partially enclosed by leaf sheaths.

*Culm aspect.*—Erect and rigid, all extending out from the ground.

*Culm color.*—Green (RHS 143A through 144 C), with the paler green colors toward the base of the culm.

*Culm size.*—About a ¼ to ⅜ inch wide, tapered toward the top at 4 to 6 feet high in mature plants.

*Culm surface.*—Glabrous, although some hair appears in varying areas.

*Internode length.*—The spacing between leaves extending out from the culm vary, but the spacing does not exceed 10 inches.

*Ligule.*—There is no ligule.

Foliage description:

*Leaf shape.*—Linear.

*Leaf division.*—Simple.

*Leaf base.*—Sheathed.

*Leaf apex.*—Acute.

*Leaf aspect.*—Leaves emerge erect, and diverge from leaf sheath at an angle in the range between 30° and 40° from culm center. Leaves are concave with respect to the culm.

*Leaf venation.*—A mid rib extends through entire leaf. The mid rib is recessed and the color is white (RHS NN155C through NN155D).

*Leaf margins.*—Straight.

*Leaf persistence.*—Leaves dry out in winter but remain attached to the culm.

*Leaf attachment.*—Sheathed. Leaf blade extends out from a sheath.

*Leaf size.*—Up to 36 inches in length and ½ inch in width.

*Leaf surface.*—Glabrous on the upper and lower surfaces with faint ribbing extending parallel to the mid rib.

*Leaf number.*—About 12-14 per culm.

*Leaf color.*—Leaves are banded with alternating green and yellow bands. The banding is limited to the leaves and does not occur in culm. There are four to seven yellow bands per leaf blade. When mature, the bands extend the entire width of the leaf blade and the yellow bands are approximately one inch in length. The range of yellow color in the yellow bands extends between RHS 5A and 5D. The mid rib is NN155C through NN155D and the green bands extend from N137A through N137B. The banding color extends through the leaf and is visible on both sides of the leaf blade. The banding colors on the back side of the leaf are the same as on the front side of the leaf.

Flower description: The flower is a single stalk having a yellow green color (RHS 148C). Inflorescence extends out from the stalk loosely comprising a panicle of 18-24 spikelets. The seeds, measuring approximately 1 mm in length and having a reddish purple color (RHS 72 through A72B), extend along the spikelets. With approximately 40 seeds per spikelet, each culm will produce approximately between 720 and 960 seeds.

Figure 4:
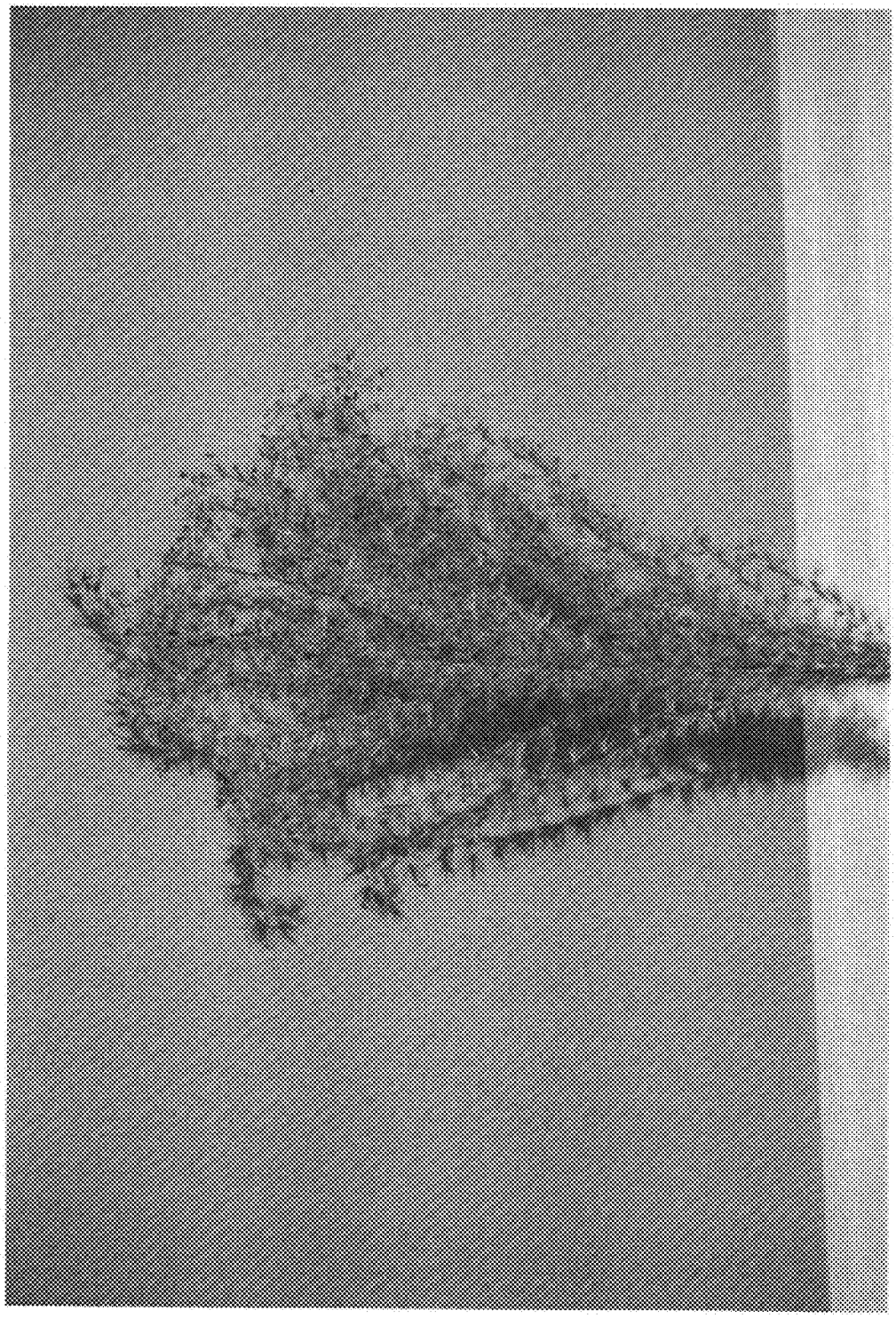
FIG. 4 is a close-up photograph of the bloom with hairs of the seeds visible.

Caryopsis: Seeds extend along the spikelets with a pericarp having a color in the range of RHS 72 through A72B. Removal of the pericarp releases short hairs (FIG. 4) that circumscribe the seed to aid the transportation of the seed. It has not been determined whether the seeds are viable.

I claim:

1. A new and distinct cultivar of *Miscanthus* plant named 'Tiger Tail' as herein illustrated and described.

* * * * *